US007026354B2

(12) United States Patent
Syverson et al.

(10) Patent No.: US 7,026,354 B2
(45) Date of Patent: Apr. 11, 2006

(54) AROMATIC COMPOSITIONS FOR THE INHIBITION OF EXOPROTEIN PRODUCTION FROM GRAM POSITIVE BACTERIA

(75) Inventors: Rae Ellen Syverson, Fond du Lac, WI (US); Richard A. Proctor, Madison, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/969,218

(22) Filed: Oct. 2, 2001

(65) Prior Publication Data

US 2003/0134897 A1 Jul. 17, 2003

(51) Int. Cl.

*A61K 31/27* (2006.01)
*A61K 31/24* (2006.01)
*A62D 3/00* (2006.01)
*A01N 25/02* (2006.01)

(52) U.S. Cl. .................. 514/476; 435/252.1; 424/401; 424/405

(58) Field of Classification Search ................ 424/404, 424/402, 401, 405; 514/546, 534, 476; 435/252.1
See application file for complete search history.

(56) References Cited

U.S. PATENT DOCUMENTS

| | | | | |
|---|---|---|---|---|
| 3,317,376 | A | | 5/1967 | Schattner |
| 4,405,323 | A | | 9/1983 | Auerbach |
| 4,413,032 | A | | 11/1983 | Hartmann et al. |
| 4,413,986 | A | | 11/1983 | Jacobs |
| 4,424,054 | A | | 1/1984 | Conn et al. |
| 4,431,427 | A | | 2/1984 | Lefren et al. |
| 4,560,549 | A | | 12/1985 | Ritchey |
| 4,582,717 | A | | 4/1986 | von Bittera et al. |
| 4,585,792 | A | | 4/1986 | Jacob et al. |
| 4,722,936 | A | | 2/1988 | Jacob |
| 4,722,937 | A | | 2/1988 | Jacob et al. |
| 4,769,021 | A | | 9/1988 | Kass |
| 4,952,211 | A | | 8/1990 | Snider |
| 5,000,749 | A | | 3/1991 | Leveen et al. |
| 5,070,889 | A | | 12/1991 | Leveen et al. |
| 5,071,648 | A | | 12/1991 | Rosenblatt |
| 5,156,164 | A | | 10/1992 | Leveen et al. |
| 5,180,749 | A | | 1/1993 | Cusack et al. |
| 5,221,693 | A | | 6/1993 | Shetty |
| 5,292,532 | A | * | 3/1994 | Bombart ..................... 424/405 |
| 5,342,331 | A | | 8/1994 | Silber et al. |
| 5,389,374 | A | | 2/1995 | Brown-Skrobot |
| 5,476,455 | A | | 12/1995 | Silber |
| 5,498,252 | A | | 3/1996 | Silber |
| 5,527,892 | A | | 6/1996 | Borsotti et al. |
| 5,540,979 | A | | 7/1996 | Yahiaoui et al. |
| 5,547,985 | A | | 8/1996 | Brown-Skrobot et al. |
| 5,601,814 | A | | 2/1997 | Barton et al. |
| 5,612,045 | A | | 3/1997 | Syverson |
| 5,618,554 | A | | 4/1997 | Syverson |
| 5,641,503 | A | | 6/1997 | Brown-Skrobot |
| 5,643,582 | A | * | 7/1997 | Gangadharan et al. ...... 424/401 |
| 5,679,369 | A | | 10/1997 | Brown-Skrobot |
| 5,685,872 | A | | 11/1997 | Syverson |
| 5,705,182 | A | | 1/1998 | Brown-Skrobot |

(Continued)

FOREIGN PATENT DOCUMENTS

EP 0 009 977 A1 4/1980

(Continued)

OTHER PUBLICATIONS

Osol, A. et al. (eds.), 1980. Remington's Pharmaceutical Sciences. 16th Edition. Philadelphia College of Pharmacy and Science. p. 999.*

(Continued)

*Primary Examiner*—Ralph Gitomer
*Assistant Examiner*—Kailash C. Srivastava
(74) *Attorney, Agent, or Firm*—Senniger Powers

(57) ABSTRACT

Compositions including an aromatic compound for inhibiting the production of exoproteins by Gram positive bacteria are disclosed. The aromatic inhibitory compounds of the present invention have the general formula:

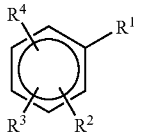

wherein $R^1$ is selected from the group consisting of H,

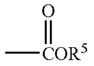

—$OR^5$, —$R^6C(O)H$, —$R^6OH$, —$R^6COOH$, —$OR^6OH$, —$OR^6COOH$, —$C(O)NH_2$,

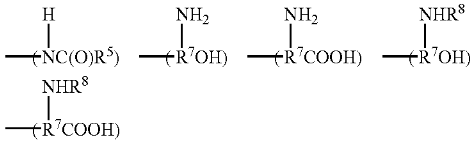

and $NH_2$ and salts thereof; $R^5$ is a monovalent saturated or unsaturated aliphatic hydrocarbyl moiety; $R^6$ is a divalent saturated or unsaturated aliphatic hydrocarbyl moiety; $R^7$ is a trivalent saturated or unsaturated aliphatic hydrocarbyl moiety; $R^8$ is a monovalent substituted or unsubstituted saturated or unsaturated aliphatic hydrocarbyl moiety which may or may not be interrupted with hetero atoms; $R^2$, $R^3$, and $R^4$ are independently selected from the group consisting of H, OH, COOH, and —$C(O)R^9$; $R^9$ is hydrogen or a monovalent saturated or unsaturated aliphatic hydrocarbyl moiety.

5 Claims, No Drawings

U.S. PATENT DOCUMENTS

| | | | | |
|---|---|---|---|---|
| 5,728,690 | A * | 3/1998 | Chen | 514/179 |
| 5,753,252 | A | 5/1998 | Brown-Skrobot | |
| 5,770,543 | A | 6/1998 | Garst et al. | |
| 5,814,567 | A | 9/1998 | Yahiaoui et al. | |
| 5,817,047 | A | 10/1998 | Osborn, III et al. | |
| 5,895,643 | A | 4/1999 | Hoppe et al. | |
| 5,898,030 | A * | 4/1999 | Samaritani | 514/12 |
| 5,932,495 | A | 8/1999 | Boney et al. | |
| 5,945,175 | A | 8/1999 | Yahiaoui et al. | |
| 6,017,832 | A | 1/2000 | Yahiaoui et al. | |
| 6,028,016 | A | 2/2000 | Yahiaoui et al. | |
| 6,039,716 | A | 3/2000 | Jessup et al. | |
| 6,060,636 | A | 5/2000 | Yahiaoui et al. | |
| 6,224,886 | B1 | 5/2001 | Charlton et al. | |
| 6,294,186 | B1 | 9/2001 | Beerse et al. | |
| 6,416,779 | B1 | 7/2002 | D'Augustine et al. | |
| 6,767,508 | B1 | 7/2004 | Yahiaoui et al. | |

FOREIGN PATENT DOCUMENTS

| | | | |
|---|---|---|---|
| EP | 0 053 221 | A2 | 6/1982 |
| EP | 0 110 793 | B1 | 6/1984 |
| EP | 0 391 741 | A2 | 10/1990 |
| EP | 0 395 099 | A2 | 10/1990 |
| EP | 0 483 812 | B1 | 5/1992 |
| EP | 0 483 835 | A1 | 5/1992 |
| EP | 0 683 260 | A2 | 2/1995 |
| GB | 1068667 | | 5/1967 |
| GB | 2 186 486 | A | 8/1987 |
| JP | 08245907 | A | 9/1996 |
| WO | WO 87/03208 | A1 | 6/1987 |
| WO | WO 94/22501 | A1 | 10/1994 |
| WO | WO 96/40300 | A2 | 12/1996 |
| WO | WO 98/09662 | A1 | 3/1998 |
| WO | WO 98/41179 | A1 | 9/1998 |
| WO | WO 99/12505 | A2 | 3/1999 |
| WO | WO 99/38541 | A1 | 8/1999 |
| WO | WO 99/61079 | A1 | 12/1999 |

OTHER PUBLICATIONS

Matsumura et al., Surface Activities, Biodegradability and Antimicrobial Properties of n-Alkyl Glucosides, Mannosides and Galactosides, *J. Amer. Oil Chem. Soc.*, Dec. 1990, pp. 996-1000, vol. 67.

PCT/US02/28756 PCT International Search Report completed Dec. 18, 2002.

* cited by examiner

AROMATIC COMPOSITIONS FOR THE INHIBITION OF EXOPROTEIN PRODUCTION FROM GRAM POSITIVE BACTERIA

BACKGROUND OF THE INVENTION

The present invention relates to the inhibition of exoprotein production from Gram positive bacteria. More particularly, the present invention relates to compositions comprising aromatic compounds and the effects of these compounds on Gram positive bacteria. The present invention also relates to methods of using these aromatic containing compositions.

There exists in the female body a complex process which maintains the vagina and physiologically related areas in a healthy state. In a female between the age of menarche and menopause, the normal vagina provides an ecosystem for a variety of microorganisms. Bacteria are the predominant type of microorganism present in the vagina; most women harbor about $10^9$ bacteria per gram of vaginal fluid. The bacterial flora of the vagina is comprised of both aerobic and anaerobic bacteria. The more commonly isolated bacteria are *Lactobacillus* species, *Corynebacteria, Gardnerella vaginalis, Staphylococcus* species, *Peptococcus* species, aerobic and anaerobic *Streptococcus* species, and *Bacteroides* species. Other microorganisms that have been isolated from the vagina on occasion include yeast (*Candida albicans*), protozoa (*Trichomonas vaginalis*), mycoplasma (*Mycoplasma hominis*), chlamydia (*Chlamydia trachomatis*), and viruses (*Herpes simplex*). These latter organisms are generally associated with vaginitis or venereal disease, although they may be present in low numbers without causing symptoms.

Physiological, social, and idiosyncratic factors effect the quantity and species of bacteria present in the vagina. Physiological factors include age, day of the menstrual cycle, and pregnancy. For example, vaginal flora present in the vagina throughout the menstrual cycle can include *lactobacilli, corynebacterium*, ureaplasma, and mycoplasma. Social and idiosyncratic factors include method of birth control, sexual practices, systemic disease (e.g., diabetes), and medications.

Bacterial proteins and metabolic products produced in the vagina can effect other microorganisms and the human host. For example, the vagina between menstrual periods is mildly acidic having a pH ranging from about 3.8 to about 4.5. This pH range is generally considered the most favorable condition for the maintenance of normal flora. At that pH, the vagina normally harbors the numerous species of microorganisms in a balanced ecology, playing a beneficial role in providing protection and resistance to infection and makes the vagina inhospitable to some species of bacteria such as *Staphylococcus aureus* (*S. aureus*). The low pH is a consequence of the growth of *lactobacilli* and their production of acidic products. Microorganisms in the vagina can also produce antimicrobial compounds such as hydrogen peroxide and bactericides directed at other bacterial species. One example is the lactocins, bacteriocin-like products of *lactobacilli* directed against other species of *lactobacilli.*

Some microbial products produced in the vagina may negatively affect the human host. For example, *S. aureus* can produce and excrete into its environment a variety of exoproteins including enterotoxins, Toxic Shock Syndrome Toxin-1 (TSST-1), and enzymes such as proteases and lipase. When absorbed into the bloodstream of the host, TSST-1 may produce Toxic Shock Syndrome (TSS) in non-immune humans.

*S. aureus* is found in the vagina of approximately 16% of healthy women of menstrual age. Approximately 25% of the *S. aureus* isolated from the vagina are found to produce TSST-1. TSST-1 and some of the staphylococcal enterotoxins have been identified as causing TSS in humans.

Symptoms of Toxic Shock Syndrome generally include fever, diarrhea, vomiting and a rash followed by a rapid drop in blood pressure. Multiple organ failure occurs in approximately 6% of those who contract the disease. *S. aureus* does not initiate Toxic Shock Syndrome as a result of the invasion of the microorganism into the vaginal cavity. Instead as *S. aureus* grows and multiplies, it can produce TSST-1. Only after entering the bloodstream does TSST-1 toxin act systemically and produce the symptoms attributed to Toxic Shock Syndrome.

Menstrual fluid has a pH of about 7.3. During menses, the pH of the vagina moves toward neutral and can become slightly alkaline. This change permits microorganisms whose growth is inhibited by an acidic environment the opportunity to proliferate. For example, *S. aureus* is more frequently isolated from vaginal swabs during menstruation than from swabs collected between menstrual periods.

When *S. aureus* is present in an area of the human body that harbors a normal microbial population such as the vagina, it may be difficult to eradicate the *S. aureus* bacterium without harming members of the normal microbial flora required for a healthy vagina. Typically, antibiotics that kill *S. aureus* are not an option for use in catamenial products because of their effect on the normal vaginal microbial flora and their propensity to stimulate toxin production if all of the *S. aureus* are not killed. An alternative to eradication is technology designed to prevent or substantially reduce the bacterium's ability to produce toxins.

There have been numerous attempts to reduce or eliminate pathogenic microorganisms and menstrually occurring Toxic Shock Syndrome by incorporating into a tampon pledget one or more biostatic, biocidal, and/or detoxifying compounds. For example, L-ascorbic acid has been applied to a menstrual tampon to detoxify toxin found in the vagina. Others have incorporated monoesters and diesters of polyhydric aliphatic alcohols, such as glycerol monolaurate, as biocidal compounds (see, e.g., U.S. Pat. No. 5,679,369). Still others have introduced other non-ionic surfactants, such as alkyl ethers, alkyl amines, and alkyl amides as detoxifying compounds (see, e.g., U.S. Pat. Nos. 5,685,872, 5,618,554, and 5,612,045).

Despite the aforementioned art, there continues to be a need for compositions and methods for using the compositions that will effectively inhibit the production of exoproteins, such as TSST-1, from Gram positive bacteria, and maintain activity even in the presence of the enzymes lipase and esterase which can have adverse effects on potency and which may also be present in the vagina. Further, it is desirable that the compositions useful in the inhibition of the production of exoproteins be substantially non-harmful to the natural flora found in the vaginal area.

SUMMARY OF THE INVENTION

The present invention is based on the discovery that aromatic compounds having the general structure:

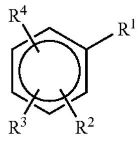

wherein $R^1$ is selected from the group consisting of H,

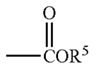

—$OR^5$, —$R^6C(O)H$, —$R^6OH$, —$R^6COOH$, —$OR^6OH$, —$OR^6COOH$, —$C(O)NH_2$,

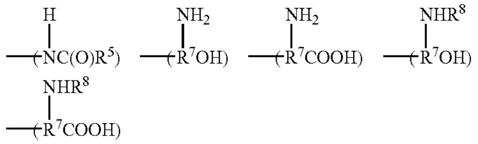

and $NH_2$ and salts thereof; $R^5$ is a monovalent saturated or unsaturated aliphatic hydrocarbyl moiety; $R^6$ is a divalent saturated or unsaturated aliphatic hydrocarbyl moiety; $R^7$ is a trivalent saturated or unsaturated aliphatic hydrocarbyl moiety; $R^8$ is a monovalent substituted or unsubstituted saturated or unsaturated aliphatic hydrocarbyl moiety which may or may not be interrupted with hetero atoms; $R^2$, $R^3$, and $R^4$ are independently selected from the group consisting of H, OH, COOH, and —$C(O)R^9$; $R^9$ is hydrogen or a monovalent saturated or unsaturated aliphatic hydrocarbyl moiety, are particularly effective for inhibiting the production of exoprotein(s) of Gram positive bacteria. The present invention relates to compositions incorporating these aromatic compounds and methods for using these aromatic-containing compositions to inhibit the production of exoproteins from Gram positive bacteria.

It is a general object of the present invention to provide a composition for use in inhibiting the production of exoproteins from Gram positive bacteria. The compositions of the present invention are particularly useful for inhibiting the production of TSST-1, Enterotoxin B and alpha hemolysin from *S. aureus* bacteria. The compositions, which comprise one or more aromatic compounds as described herein and a pharmaceutically acceptable carrier, can be prepared and applied to a substrate or product in a variety of suitable forms, including without limitation, aqueous solutions, lotions, balms, gels, salves, ointments, boluses, suppositories, and the like. In one embodiment, the active aromatic compound of the composition can be formulated into a variety of vaginal cleaning formulations, such as those employed in current commercial douche formulations, or in higher viscosity douches.

Another object of the present invention is to provide methods for using the aromatic containing compositions of the present invention. The methods as described herein comprise exposing Gram positive bacteria to an effective amount of an aromatic containing composition such that the Gram positive bacteria is substantially inhibited from producing exoproteins.

Other objects and advantages of the present invention, and modifications thereof, will become apparent to persons skilled in the art without departure from the inventive concepts defined in the claims.

DETAILED DESCRIPTION OF THE PREFERRED EMBODIMENTS

In accordance with the present invention, it has been discovered that aromatic-containing compositions as described herein, when exposed to *S. aureus* or other Gram positive bacteria, can reduce the production of harmful exoproteins, such as TSST-1, Enterotoxin B and alpha hemolysin. It has also been discovered that the aromatic-containing compositions can be used in combination with surface-active agents such as, for example, compounds with an ether, ester, amide, glycosidic, or amine bond linking a $C_8$–$C_{18}$ fatty acid to an aliphatic alcohol, polyalkoxylated sulfate salt, or polyalkoxylated sulfosuccinic salt, to substantially inhibit the production of exoproteins such as TSST-1 from Gram positive bacteria.

The aromatic-containing compositions of the present invention comprise an aromatic compound having the general chemical structure:

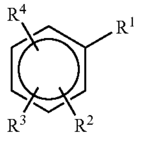

wherein $R^1$ is selected from the group consisting of H,

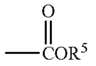

—$OR^5$, —$R^6C(O)H$, —$R^6OH$, —$R^6COOH$, —$OR^6OH$, —$OR^6COOH$, —$C(O)NH_2$,

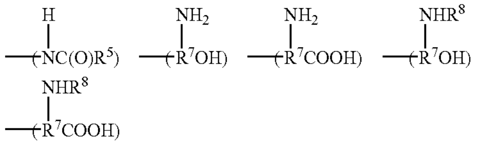

and $NH_2$ and salts thereof; $R^5$ is a monovalent saturated or unsaturated aliphatic hydrocarbyl moiety; $R^6$ is a divalent saturated or unsaturated aliphatic hydrocarbyl moiety; $R^7$ is a trivalent saturated or unsaturated aliphatic hydrocarbyl moiety; $R^8$ is hydrogen or a monovalent substituted or unsubstituted saturated or unsaturated aliphatic hydrocarbyl moiety which may or may not be interrupted with hetero atoms; $R^2$, $R^3$, and $R^4$ are independently selected from the group consisting of H, OH, COOH, and —$C(O)R^9$; $R^9$ is a monovalent saturated or unsaturated aliphatic hydrocarbyl moiety.

The hydrocarbyl moieties described herein include both straight chain and branched chain hydrocarbyl moieties and may or may not be substituted and/or interrupted with hetero atoms. Desirably, the aromatic compounds for use in the present invention contain at least one OH and/or COOH group. The OH and/or COOH group can be bonded to the aromatic structure, or can be bonded to an atom which may or may not be directly bonded to the aromatic structure. $R^5$ is desirably a monovalent saturated aliphatic hydrocarbyl moiety having from 1 to about 15 carbon atoms, preferably from 1 to about 14 carbon atoms. $R^6$ is desirably a divalent saturated or unsaturated aliphatic hydrocarbyl moiety having from 1 to about 15 carbon atoms, preferably from 1 to about 14 carbon atoms. $R^7$ is desirably a trivalent saturated or unsaturated aliphatic hydrocarbyl moiety having from 1 to about 15 carbon atoms, preferably from 1 to about 10 carbon atoms, and more preferably from 1 to about 4 carbon atoms. Hetero atoms which can interrupt the hydrocarbyl moiety include, for example, oxygen and sulfur.

Preferred aromatic compounds of the present invention include 2-phenylethanol, benzyl alcohol, trans-cinnamic acid, 4-hydroxybenzoic acid methyl ester, 2-hydroxybenzoic acid, 2-hydoxybenzamide, acetyl tyrosine, 3,4,5-trihydroxybenzoic acid, lauryl 3,4,5-trihydroxybenzoate, phenoxyethanol, 4-hydroxy-3-methoxybenzoic acid, p-aminobenzoic acid, and 4-acetamidophenol.

In accordance with the present invention, the compositions including the aromatic compound(s) contain an effective amount of the inhibiting aromatic compound to substantially inhibit the formation of TSST-1 when the composition is exposed to *S. aureus* bacteria. Several methods are known in the art for testing the effectiveness of potential inhibitory agents for the inhibition of the production of TSST-1 in the presence of *S. aureus*. One such preferred method is set forth in Example 1 below. When tested in accordance with the testing methodology described herein, the inhibiting aromatic compounds reduce the formation of TSST-1 when the composition is exposed to *S. aureus* by at least about 40%, more desirably by at least about 50%, still more desirably by at least about 60%, still more desirably by at least about 70%, still more desirably by at least about 80%, still more desirably by at least about 90%, and still more desirably by at least about 95%.

Where the aromatic compound is formulated as a composition which includes a pharmaceutically acceptable carrier, the composition typically contains at least about 0.01% (volume/volume) and desirably at least about 0.04% (volume/volume) aromatic compound (based on the total volume of the composition). Typically, the composition will contain no more than about 1.0% (volume/volume) of aromatic compound. One skilled in the art will recognize that the concentration of aromatic compound will vary depending upon the compound selected and the other components of the formulation. Particularly suitable formulations for use in vaginal cleansing applications can contain at least about 0.20 millimoles/liter, and desirably no more than about 50 millimoles/liter. Desirably, vaginal cleansing formulations contain from about 0.3 millimoles/liter to about 30 millimoles/liter of aromatic compound or from about 1 millimoles/liter to about 15 millimoles/liter of aromatic compound.

The amount of aromatic compound used in a specific application will depend upon the particular form and/or use of the composition. The actual amount can be readily selected by those skilled in the art based on the teaching contained herein. For example, a catamenial tampon designed to be inserted into a body cavity and subsequently in intimate contact with the vaginal epithelium may require less aromatic compound than an absorbent article such as a bandage worn exterior to the body. In another example, a catemenial tampon designed to absorb menstrual fluid may require more aromatic compound than a liquid formulation intended for direct vaginal application.

The aromatic compositions of the present invention may contain other additives as appropriate for a desired result so long as the additives do not have a substantially antagonistic effect on the activity of the aromatic compounds. Examples of such additives include conventional surfactants such as ethoxylated hydrocarbons or surfactants, or co-wetting aids such as low molecular weight alcohols.

As will be recognized by those skilled in the art, many types of substrates may be treated with the aromatic compositions of the present invention including nonwovens such as spunbond, meltblown, carded webs and others as well as woven webs and even films and the like. It will also be recognized by those skilled in the art that some aromatic compounds may be used as an internal additive or added to the polymer melt directly or in a concentrate form. After fiber formation, such additives can migrate to the fiber surface and impart the desired effect. Such internal addition of additives is discuss in U.S. Pat. No. 5,540,979 which is incorporated by reference.

The aromatic-containing compositions of the present invention may be applied to articles using conventional methods for applying an inhibitory agent to the desired article. For example, unitary tampons without separate wrappers may be dipped directly into a liquid bath having the composition and can then be air dried if necessary to remove any volatile solvents. For compressed tampons, impregnating of any of its elements is typically done prior to compressing. The compositions when incorporated on and/or into the tampon materials may be fugitive, loosely adhered, bound, or any combination thereof. As used herein, the term "fugitive" means that the composition is capable of migrating through the tampon materials. For example, the aromatic compound may be blended together with a polymeric material that is to be processed into a component of an absorbent or non-absorbent product.

In another embodiment, an aromatic containing composition may be applied directly onto an individual layer of material before it is incorporated into an article to be manufactured, such as an absorbent product. For example, an aqueous solution containing the aromatic compound can be sprayed onto the surface of a porous cover sheet or absorbent layer designed to be incorporated into an absorbent product. This can be done either during the production of the individual layer or during a fabrication process which incorporates the layer into the article being manufactured.

Nonwoven webs coated with the aromatic-containing compositions of the present invention can be prepared by conventional processes. For example, the aromatic composition can be applied to one or both sides of a traveling web. It will be appreciated by those skilled in the art that the application can be carried out as an inline treatment or as a separate, offline step. A web, such as a spunbond or meltblown nonwoven, can be directed over support rolls to a treating station including rotary spray heads for application to one side of the web. An optional treating station may include rotary spray heads to apply aromatic composition to the opposite side of the web. Each treatment station typically receives a supply of treating liquid from a reservoir. The treated web may then be dried if needed by passing over dryer cans or other drying means and then wound as a roll or converted to the use of which it is intended. Alternative drying means such as ovens, through air dryers, infra red dryers, air blowers, and the like may also be utilized.

The compositions of the present invention can be prepared and applied in numerous forms including, without limitation, aqueous solutions, lotions, balms, gels, salves, ointments, boluses, suppositories, and the like. For example, the active component of the compositions of this invention can be formulated into a variety of formulations such as those employed in current commercial douche formulations, or in higher viscosity douches. The compositions may also be formulated with surfactants, preservatives, and viscosity effecting agents.

The compositions may additionally employ one or more conventional pharmaceutically-acceptable and compatible carrier materials useful for the desired application. The carrier can be capable of co-dissolving or suspending the materials used in the composition. Carrier materials suitable for use in the instant compositions include those well-known for use in the cosmetic and medical arts as a basis for ointments, lotions, creams, salves, aerosols, suppositories, gels and the like. A suitable carrier can be comprised of alcohol and/or surfactants, for example.

The aromatic compounds of the present invention may additionally employ adjunct components conventionally found in pharmaceutical compositions in their art-established fashion and at their art-established levels. For example, the compositions may contain additional compatible pharmaceutically active materials for combination therapy, such as supplementary antimicrobial, antioxidants, anti-parasitic agents, antipruritics, astringents, local anaesthetics, or anti-inflammatory agents. As used herein, the term “compatible” means that the added component is not substantially antagonistic to the aromatic active compound.

In another embodiment of the present invention, compositions comprising the inhibitory aromatic compounds described above can further comprise with one or more surface active agents to reduce the production of TSST-1 without significantly eliminating the beneficial bacterial flora. The surface active agents can include, for example, compounds with an ether, ester, amide, glycosidic, or amine bond linking a $C_8$–$C_{18}$ fatty acid to an aliphatic alcohol, polyalkoxylated sulfate salt, or polyalkoxylated sulfosuccinic salt.

In one embodiment, the compositions comprising the inhibitory aromatic compounds described herein can also comprise one or more ether compounds having the general formula:

$$R^{10}—O—R^{11}$$

wherein $R^{10}$ is a straight or branched alkyl or alkenyl group having a chain of from about 8 to about 18 carbon atoms and $R^{11}$ is selected from an alcohol, a polyalkoxylated sulfate salt or a polyalkoxylated sulfosuccinate salt.

The alkyl, or the $R^{10}$ moiety of the ether compounds useful for use in combination with the inhibitory aromatic compounds described herein, can be obtained from saturated and unsaturated fatty acid compounds. Suitable compounds include, $C_8$–$C_{18}$ fatty acids, and preferably, fatty acids include, without limitation, caprylic, capric, lauric, myristic, palmitic and stearic acid whose carbon chain lengths are 8, 10, 12, 14, 16, and 18, respectively. Highly preferred materials include capric, lauric, and myristic acids.

Preferred unsaturated fatty acids are those having one or two cis-type double bonds and mixtures of these materials. Suitable materials include myrystoleic, palmitoleic, linolenic and mixtures thereof.

Desirably, the $R^{11}$ moiety is an aliphatic alcohol which can be ethoxylated or propoxylated for use in the ether compositions in combination with the inhibitory aromatic compounds described herein. Suitable aliphatic alcohols include glycerol, sucrose, glucose, sorbitol and sorbitan. Preferred ethoxylated and propoxylated alcohols include glycols such as ethylene glycol, propylene glycol, polyethylene glycol and polypropylene glycol.

The aliphatic alcohols can be ethoxylated or propoxylated by conventional ethoxylating or propoxylating compounds and techniques. The compounds are preferably selected from the group consisting of ethylene oxide, propylene oxide, and mixtures thereof, and similar ringed compounds which provide a material which is effective.

The $R^{11}$ moiety can further include polyalkoxylated sulfate and polyalkoxylated sulfosuccinate salts. The salts can have one or more cations. Preferably, the cations are sodium, potassium or both.

Preferred ether compounds for use in combination with the inhibitory aromatic compounds described herein include laureth-3, laureth-4, laureth-5, PPG-5 lauryl ether, 1-0-dodecyl-rac-glycerol, sodium laureth sulfate, potassium laureth sulfate, disodium laureth (3) sulfosuccinate, dipotassium laureth (3) sulfosuccinate, and polyethylene oxide (2) sorbitol ether.

In accordance with the present invention, the composition contains an effective amount of the combination of the inhibitory aromatic and ether compounds. The amount of ether compound included in the composition is at least about 0.01% (weight/volume) and desirably at least about 0.04% (weight/volume) (based on the total volume of the composition). Typically, the composition contains no more than about 0.3% (weight/volume) ether compound. Particularly suitable formulations for use in vaginal cleansing applications will contain at least about 0.25 millimoles/liter, desirably no more than about 10 millimoles/liter, and most desirably from about 0.5 millimoles/liter to about 5 millimoles/liter of ether compound.

The compositions of the present invention containing a first inhibitory aromatic compound and a second inhibitory ether compound contain a sufficient amount of both inhibitory compounds to substantially inhibit the formation of TSST-1 when the composition is exposed to *S. aureus* bacteria. Preferably, the combination of inhibitory compounds reduces the formation of TSST-1 when the composition is exposed to *S. aureus* by at least about 40%, more preferably at least about 50%, still more preferably at least about 60%, still more preferably by at least about 70%, still more preferably by at least about 80%, still more preferably by at least about 90%, and still more preferably by at least about 95%.

Typically, the composition will contain a molar ratio of inhibitory aromatic compound to ether compound of from about 1:6 to about 1:0.05.

In another embodiment, the compositions comprising the inhibitory aromatic compounds described herein can also comprise one or more alkyl polyglycoside compounds. Suitable alkyl polyglycosides for use in combination with the inhibitory aromatic compounds include alkyl polyglycosides having the general formula:

$$H\text{-}(Z_n)\text{-}O—R^{14}$$

wherein Z is a saccharide residue having 5 or 6 carbon atoms, n is a whole number from 1 to 6, and $R^{14}$ is a linear or branched alkyl group having from about 8 to about 18 carbon atoms. Commercially available examples of suitable alkyl polyglycosides having differing carbon chain lengths include Glucopon 220, 225, 425, 600, and 625, all available from Henkel Corporation (Ambler, Pa.). These products are all mixtures of alkyl mono- and oligoglucopyranosides with differing alkyl group chain lengths based on fatty alcohols derived from coconut and/or palm kernel oil. Glucopon 220, 225, and 425 are examples of particularly suitable alkyl polyglycosides for use in combination with the inhibitory aromatic compounds of the present invention. Another example of a suitable commercially available alkyl polyglycoside is TL 2141, a Glucopon 220 analog available from ICI Surfactants (Wilmington, Del.).

It should be understood that as referred to herein, an alkylpolyglycoside may consist of a single type of alkyl polyglycoside molecule or, as is typically the case, may include a mixture of different alkyl polyglycoside molecules. The different alkyl polyglycoside molecules may be isomeric and/or may be alkyl polyglycoside molecules with differing alkyl group and/or saccharide portions. By use of the term alkyl poyglycoside isomers reference is made to alkyl polyglycosides which, although including the same alky ether residues, may vary with respect to the location of the alkyl ether residue in the alkyl polyglycoside as well as isomers which differ with respect to the orientation of the functional groups about one or more chiral centers in the molecules. For example, an alkyl polyglycoside can include a mixture of molecules with saccharide portions which are mono, di-, or oligosaccharides derived from more than one 6 carbon saccharide residue and where the mono-, di- or oligosaccharide has been etherified by reaction with a mixture of fatty alcohols of varying carbon chain length. The present alkyl polyglycosides desirably include alkyl groups where the average number of carbon atoms in the alkyl chain is about 8 to about 12. One example of a suitable alkyl polyglycoside is a mixture of alkyl polyglycoside molecules with alkyl chains having from about 8 to about 10 carbon atoms.

The alkyl polyglycosides employed in the compositions in combination with the inhibiting aromatic compounds can be characterized in terms of their hydrophilic lipophilic balance (HLB). This can be calculated based on their chemical structure using techniques well known to those skilled in the art. The HLB of the alkyl polyglycosides used in the present invention typically falls within the range of about 10 to about 15. Desirably, the present alkyl polyglycosides have an HLB of at least about 12 and, more desirably, about 12 to about 14.

The compositions of the present invention containing a first inhibitory aromatic compound and a second inhibitory alkyl polyglycoside compound contain a sufficient amount of both inhibitory compounds to substantially inhibit the formation of TSST-1 when the composition is exposed to *S. aureus* bacteria. Preferably, the combination of inhibitory compounds reduces the formation of TSST-1 when the composition is exposed to *S. aureus* by at least about 40%, more preferably at least about 50%, still more preferably at least about 60%, still more preferably by at least about 70%, still more preferably by at least about 80%, still more preferably by at least about 90%, and still more preferably by at least about 95%.

In accordance with the present invention, the composition contains an effective amount of the combination of the inhibitory aromatic and alkyl polyglycoside compounds. The amount of alkyl polyglycoside compound included in the composition is at least about 0.01% (weight/volume) and desirably at least about 0.04% (weight/volume) (based on the total volume of the composition). Typically, the composition contains no more than about 0.3% (weight/volume) alkyl polyglycoside compound. Particularly suitable formulations for use in vaginal cleansing applications will contain at least about 0.25 millimoles/liter, desirably no more than about 5 millimoles/liter, and most desirably from about 0.5 to about 3 millimoles/liter of alkyl polyglycoside compound.

Typically, the composition will contain a molar ratio of inhibitory aromatic compound to alkyl glycoside compound of from about 1:1 to about 1:0.005.

In another embodiment, the aromatic-containing compositions of the present invention can further comprise an amide containing compound having the general formula:

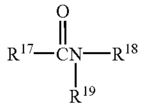

wherein $R^{17}$, inclusive of the carbonyl carbon, is an alkyl group having 8 to 18 carbon atoms, and $R^{18}$ and $R^{19}$ are independently selected from hydrogen or an alkyl group having from 1 to about 12 carbon atoms which may or may not be substituted with groups selected from ester groups, ether groups, amine groups, hydroxyl groups, carboxyl groups, carboxyl salts, sulfonate groups, sulfonate salts, and mixtures thereof.

$R^{17}$ can be derived from saturated and unsaturated fatty acid compounds. Suitable compounds include, $C_8$–$C_{18}$ fatty acids, and preferably, the fatty acids include, without limitation, caprylic, capric, lauric, myristic, palmitic and stearic acid whose carbon chain lengths are 8, 10, 12, 14, 16, and 18, respectively. Highly preferred materials include capric, lauric, and myristic.

Preferred unsaturated fatty acids are those having one or two cis-type double bonds and mixtures of these materials. Suitable materials include myrystoleic, palmitoleic, linolenic and mixtures thereof.

The $R^{18}$ and $R^{19}$ moieties can be the same or different and each being selected from hydrogen and an alkyl group having a carbon chain having from 1 to about 12 carbon atoms. The $R^{18}$ and $R^{19}$ alkyl groups can be straight or branched and can be saturated or unsaturated. When $R^{18}$ and/or $R^{19}$ are an alkyl moiety having a carbon chain of at least 2 carbons, the alkyl group can include one or more substituent groups selected from ester, ether, amine, hydroxyl, carboxyl, carboxyl salts, sulfonate and sulfonate salts. The salts can have one or more cations selected from sodium, potassium or both.

Preferred amide compounds for use in combination with the inhibitory aromatic compounds described herein include sodium lauryl sarcosinate, lauramide monoethanolamide, lauramide diethanolamide, lauramidopropyl dimethylamine, disodium lauramido monoethanolamide sulfosuccinate and disodium lauroamphodiacetate.

In accordance with the present invention, the composition contains an effective amount of the combination of the inhibitory aromatic and amide compounds. The amount of amide compound included in the composition is at least about 0.01% (weight/volume) and desirably at least about 0.04% (weight/volume) (based on the total weight of the composition). Typically, the composition contains no more than about 0.3% (weight/volume) amide compound. Particularly suitable formulations for use in vaginal cleansing applications will contain at least about 0.25 millimoles/liter, desirably no more than about 5 millimoles/liter, and most desirably from about 0.5 to about 3 millimoles/liter of amide compound.

The compositions of the present invention containing a first inhibitory aromatic compound and a second inhibitory amide-containing compound contain a sufficient amount of both inhibitory compounds to substantially inhibit the formation of TSST-1 when the composition is exposed to *S. aureus* bacteria. Preferably, the combination of inhibitory compounds reduces the formation of TSST-1 when the composition is exposed to *S. aureus* by at least about 40%, more preferably at least about 50%, still more preferably at least about 60%, still more preferably by at least about 70%, still more preferably by at least about 80%, still more preferably by at least about 90%, and still more preferably by at least about 95%.

Typically, the composition will contain a molar ratio of inhibitory aromatic compound to amide-containing compound of from about 1:2 to about 1:0.05.

In another embodiment, compositions comprising the aromatic inhibitory compounds described herein can further comprise an amine compound having the following formula:

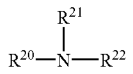

wherein $R^{20}$ is an alkyl group having from about 8 to about 18 carbon atoms and $R^{21}$ and $R^{22}$ are independently selected from the group consisting of hydrogen and alkyl groups having from 1 to about 18 carbon atoms and which can have one or more substitutional moieties selected from the group consisting of hydroxyl, carboxyl, carboxyl salts and imidazoline The combination of aromatic compounds and amine compounds are effective in substantially inhibiting the production of exoprotein from Gram positive bacteria.

Desirably, $R^{20}$ is derived from fatty acid compounds which include, without limitation, caprylic, capric, lauric, myristic, palmitic and stearic acid whose carbon chain lengths are 8, 10, 12, 14, 16, and 18, respectively. Highly preferred materials include capric, lauric, and myristic. Preferred unsaturated fatty acids are those having one or two cis-type double bonds and mixtures of these materials. Suitable materials include myrystoleic, palmitoleic, linolenic, and mixtures thereof.

The $R^{21}$ and $R^{22}$ alkyl groups can further include one or more substitutional moieties selected from hydroxyl, carboxyl, carboxyl salts, and $R^1$ and $R^2$ can form an unsaturated heterocyclic ring that contains a nitrogen that connects via a double bond to the alpha carbon of the $R^1$ moiety to form a substituted imidazoline. The carboxyl salts can have one or more cations selected from sodium potassium or both. The $R^{20}$, $R^{21}$, and $R^{22}$ alkyl groups can be straight or branched and can be saturated or unsaturated.

Preferred amine compounds for use with the aromatic compounds described herein include triethanolamide laureth sulfate, lauramine, lauramino propionic acid, sodium lauriminodipropionic acid, lauryl hydroxyethyl imidazonline and mixtures thereof.

In accordance with the present invention, the composition contains an effective amount of the combination of the inhibitory aromatic and amine compounds. The amount of amine compound in the composition is at least about 0.01% (weight/volume) and desirably at least about 0.04% (weight/volume) (based on the total weight of the composition). Typically, the composition contains no more than about 0.3% (weight/volume) ether compound. Particularly suitable formulations for use in vaginal cleansing applications will contain at least about 0.25 millimoles/liter, desirably no more than about 5 millimoles/liter, and most desirably from about 0.5 to about 3 millimoles/liter of amine compound.

The compositions of the present invention containing a first inhibitory aromatic compound and a second inhibitory amine compound contain a sufficient amount of both inhibitory compounds to substantially inhibit the formation of TSST-1 when the composition is exposed to *S. aureus* bacteria. Preferably, the combination of inhibitory compounds reduces the formation of TSST-1 when the composition is exposed to *S. aureus* by at least about 40%, more preferably at least about 50%, still more preferably at least about 60%, still more preferably by at least about 70%, still more preferably by at least about 80%, still more preferably by at least about 90%, and still more preferably by at least about 95%.

In another embodiment, the composition contains the aromatic compound and an amine salt having the general formula:

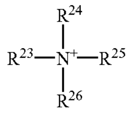

wherein $R^{23}$ is an anionic moiety associated with the amine and is derived from an alkyl group having from about 8 to about 18 carbon atoms, and $R^{24}$, $R^{25}$, and $R^{26}$ are independently selected from the group consisting of hydrogen and alkyl group having from 1 to about 18 carbon atoms and which can have one or more substitutional moieties selected from the group consisting of hydroxyl, carboxyl, carboxyl salts, and imidazoline. $R^{24}$, $R^{25}$, and $R^{26}$ can be saturated or unsaturated. Desirably, $R^{23}$ is a polyalkyloxylated alkyl sulfate. A preferred compound illustrative of an amine salt is triethanolamide laureth sulfate.

In accordance with the present invention, the composition contains an effective amount of the combination of the inhibitory aromatic and amine salt. The amount of amine salt included in the composition is at least about 0.01% (weight/volume) and desirably at least about 0.04% (weight/volume) (based on the total weight of the composition). Typically, the composition contains no more than about 0.3% (weight/volume) amine salt compound. Particularly suitable formulations for use in vaginal cleansing applications will contain at least about 0.25 millimoles/liter, desirably no more than about 5 millimoles/liter, and most desirably from about 0.5 to about 3 millimoles/liter of amine salt compound.

The compositions of the present invention containing a first inhibitory aromatic compound and a second inhibitory amine and/or amine salt compound contain a sufficient amount of both inhibitory compounds to substantially inhibit the formation of TSST-1 when the composition is exposed to *S. aureus* bacteria. Preferably, the combination of inhibitory compounds reduces the formation of TSST-1 when the composition is exposed to *S. aureus* by at least about 40%, more preferably at least about 50%, still more preferably at least about 60%, still more preferably by at least about 70%, still more preferably by at least about 80%, still more preferably by at least about 90%, and still more preferably by at least about 95%.

Typically, the composition will contain a molar ratio of inhibitory aromatic compound to amine and/or amine salt compound of from about 1:2 to about 1:0.05.

The present invention is illustrated by the following examples which are merely for the purpose of illustration and are not to be regarded as limiting the scope of the invention or manner in which it may be practiced.

EXAMPLE 1

In this Example, the effect of various test compounds on the growth of *S. aureus* and the production of TSST-1 was determined. The test compound, in the desired concentration (expressed in percent of active compound) was placed in 10 mL of a growth medium in a sterile, 50 mL conical polypropylene tube (Sarstedt, Inc. Newton, N.C.).

The growth medium was prepared by dissolving 37 grams of brain heart infusion broth (BHI) (Difco Laboratories, Cockeysville, Md.) in 880 mL of distilled water and sterilizing the broth according to the manufacturer's instructions. The BHI was supplemented with fetal bovine serum (FBS) (100 mL) (Sigma Chemical Company, St. Louis, Mo.). Hexahydrate of magnesium chloride (0.021 M, 10 mL) (Sigma Chemical Company, St. Louis, Mo.) was added to the BHI-FBS mixture. Finally, L-glutamine (0.027 M, 10 mL) (Sigma Chemical Company, St. Louis, Mo.) was added to the mixture.

Compounds to be tested included phenylethyl alcohol, benzyl alcohol, and 2-hydroxybenzamide. Test compounds were both liquids and solids. The liquid test compounds were added directly to the growth medium and diluted in growth medium to obtain the desired final concentrations. The solid test concentrations were dissolved in methanol, spectrophotometric grade (Sigma Chemical Company, St. Louis, Mo.) at a concentration that permitted the addition of 200 microliters of the solution to 10 mL of growth medium for the highest concentration tested. Each test compound that was dissolved in methanol was added to the growth medium in the amount necessary to obtain the desired final concentration.

In preparation for inoculation of the tubes of growth medium containing the test compounds, an inoculating broth was prepared as follows: *S. aureus* (MN8) was streaked onto a tryptic soy agar plate (TSA; Difco Laboratories Cockeysville, Md.) and incubated at 35° C. The test organism was obtained from Dr. Pat Schlievert, Department of Microbiology, University of Minnesota Medical School, Minneapolis, Minn. After 24 hours of incubation three to five individual colonies were picked with a sterile inoculating loop and used to inoculate 10 mL of growth medium. The tube of inoculated growth medium was incubated at 35° C. in atmospheric air. After 24 hours of incubation, the culture was removed from the incubator and mixed well on a S/P brand vortex mixer. A second tube containing 10 mL of the growth medium was inoculated with 0.5 mL of the above-described 24 hour old culture and incubated at 35° C. in atmospheric air. After 24 hours of incubation the culture was removed from the incubator and mixed well on a S/P brand vortex mixer. The optical density of the culture fluid was determined in a microplate reader (Bio-Tek Instruments, Model EL309, Winooski, Vt.). The amount of inoculum necessary to give $5\times10^6$ CFU/mL in 10 mL of growth medium was determined using a standard curve.

This Example included tubes of growth medium with varying concentrations of test compounds, tubes of growth medium without test compounds (control) and tubes of growth medium with 20–400 microliters of methanol (control). Each tube was inoculated with the amount of inoculum determined as described above. The tubes were capped with foam plugs (Identi-plug plastic foam plugs, Jaece Industries purchased from VWR Scientific Products, South Plainfield, N.J.). The tubes were incubated at 35° C. in atmospheric air containing 5% by volume $CO_2$. After 24 hours of incubation the tubes were removed from the incubator and the optical density (600 nm) of the culture fluid was determined and the culture fluid was assayed for the number of colony forming units of *S. aureus* and was prepared for the analysis of TSST-1 as described below.

The number of colony forming units per mL after incubation was determined by standard plate count procedures. In preparation for analysis of TSST-1, the culture fluid broth was centrifuged and the supernatant subsequently filter sterilized through an Autovial 5 syringeless filter, 0.2 micrometers pore size (Whatman, Inc., Clifton, N.J.). The resulting fluid was frozen at −70° C. until assayed.

The amount of TSST-1 per mL was determined by a non-competitive, sandwich enzyme-linked immunoabsorbent assay (ELISA). Samples of the culture fluid and the TSST-1 reference standard were assayed in triplicate. The method employed was as follows: four reagents, TSST-1 (#TT-606), rabbit polyclonal anti-TSST-1 IgG (LTI-101), rabbit polyclonal anti-TSST-1 IgG conjugated to horseradish peroxidase (LTC-101), and normal rabbit serum (NRS) certified anti-TSST-1 free (NRS-10) were purchased from Toxin Technology (Sarasota, Fla.). A 10 microgram/millimeter solution of the polyclonal rabbit anti-TSST-1 IgG was prepared in phosphate buffered saline (PBS) (pH 7.4). The PBS was prepared from 0.016 molar $NaH_2PO_4$, 0.004 molar $NaH_2PO_4$—$H_2O$, 0.003 molar KCl and 0.137 molar NaCl, (Sigma Chemical Company, St. Louis, Mo.). One hundred microliters of the polyclonal rabbit anti-TSST-1 IgG solution was pipetted into the inner wells of polystyrene microplates (Nunc-Denmark, Catalogue Number 439454). The plates were covered and incubated at room temperature overnight. Unbound anti-toxin was removed by draining until dry. TSST-1 was diluted to 10 nanograms/milliliter in PBS with phosphate buffered saline (pH 7.4) containing 0.05% (vol/vol) Tween-20 (PBS-Tween) (Sigma Chemical Company, St. Louis, Mo.) and 1% NRS (vol/vol) and incubated at 4° C. overnight. Test samples were combined with 1% NRS (vol/vol) and incubated at 4° C. overnight. The plates were treated with 100 microliters of a 1% solution of the sodium salt of casein in PBS (Sigma Chemical Company, St. Louis, Mo.), covered and incubated at 35° C. for one hour. Unbound BSA was removed by 3 washes with PBS-Tween. TSST-1 reference standard (10 nanograms/milliliter) treated with NRS, test samples treated with NRS, and reagent controls were pipetted in 200 microliter volumes to their respective wells on the first and seventh columns of the plate. One hundred microliters of PBS-Tween was added to the remaining wells. The TSST-1 reference standard and test samples were then serially diluted 6 times in the PBS-Tween by transferring 100 microliters from well-to-well. The samples were mixed prior to transfer by repeated aspiration and expression. This was followed by incubation for 1.5 hours at 35° C. and five washes with PBS-T and three washes with distilled water to remove unbound toxin. The rabbit polyclonal anti-TSST-1 IgG conjugated to horseradish peroxidase wash diluted according to manufacturer's instructions and 50 microliters was added to each microtiter well, except well A-1, the conjugate control well. The plates were covered and incubated at 35° C. for one hour.

Following incubation the plates were washed five times in PBS-Tween and three times with distilled water. Following the washes, the wells were treated with 100 microliters of horseradish peroxidase substrate buffer consisting of 5 milligrams of o-phenylenediamine and 5 microliters of 30% hydrogen peroxide in 11 mL of citrate buffer (pH 5.5). The citrate buffer was prepared from 0.012 M anhydrous citric acid and 0.026 molar dibasic sodium phosphate. The plates were incubated for 15 minutes at 35° C. The reaction was stopped by the addition of 50 microliters of a 5% sulfuric acid solution. The intensity of the color reaction in each well was evaluated using the BioTek Model EL309 microplate reader (OD 490 nanometers). TSST-1 concentrations in the test samples were determined from the reference toxin regression equation derived during each assay procedure. The efficacy of the compound in inhibiting the production of TSST-1 is shown in Table I below.

In accordance with the present invention, the data in Table 1 shows that *S. aureus* (MN8), when compared to the control, produced significantly less TSST-1 in the presence of the aromatic compounds. The aromatic compounds reduced the amount of exotoxin production ranging from about 91% to about 96%. However, although the amount of toxin produced was significantly reduced, there was minimal, if any, effect on the growth of *S. aureus* cells.

TABLE 1

| Compound | % Test Compound | Optical Density | CFU/mL | ELISA: TSST-1 ng/OD unit | Reduction of Toxin (%) |
|---|---|---|---|---|---|
| Growth Medium | Zero | 0.625 | 2.8E+08 | 1504 | N/A |
| Methanol | 400 μL | 0.627 | 2.8E+08 | 1440 | N/A |
| Phenylethyl alcohol | 0.5% | 0.542 | 1.6E+08 | 60 | 96% |
| Benzyl alcohol | 0.5% | 0.792 | 1.8E+08 | 131 | 91% |
| 2-hydroxybenzamide | 1.0% | 0.549 | 9.0E+07 | 65 | 95% |

N/A = Not Applicable

EXAMPLE 2

In this Example, the effect of various test compounds on the growth of *S. aureus* and the production of TSST-1 was determined. The effect of the test compounds tested in Example 2 was determined by placing the desired concentration, expressed in percent of the active compound, in 10 mL of a growth medium as described in Example 1. The test compounds were then tested and evaluated as in Example 1.

In accordance with the present invention, Table 2 shows that *S. aureus* (MN8), when compared to the control, produced significantly less TSST-1 in the presence of the aromatic compounds. The aromatic compounds reduced the amount of exotoxin production ranging from about 82% to 97%. However, although the amount of toxin produced was significantly reduced, there was minimal, if any, effect on the growth of *S. aureus* cells.

TABLE 2

| Compound | % Test Compound | Optical Density | CFU/mL | ELISA: TSST-1 ng/OD unit | Reduction of Toxin % |
|---|---|---|---|---|---|
| Growth Medium | Zero | 0.607 | >1.6E+09 | 2424 | N/A |
| Methanol | 400 μL | 0.598 | 2.6E+09 | 2690 | N/A |
| Phenylethyl alcohol | 0.5% | 0.551 | 4.2E+08 | 68 | 97% |
| Phenoxyethanol | 0.6% | 0.681 | 8.3E+08 | 70 | 97% |
| Phenoxyethanol | 0.5% | 0.728 | >1.7E+09 | 122 | 95% |
| p-hydroxybenzoic acid, methyl ester | 0.2% | 0.356 | >1.5E+08 | 506 | 82% |
| 2-hydroxybenzoic acid | 0.2% | 0.682 | 1.48E+09 | 193 | 93% |
| p-aminobenzoic acid | 0.2% | 0.618 | 1.1E+09 | 317 | 89% |

N/A = Not Applicable

EXAMPLE 3

In this Example, the effect of various test compounds on the growth of *S. aureus* and the production of TSST-1 was determined. The effect of the test compounds tested in Example 3 was determined by placing the desired concentration, expressed in percent of the active compound, in 10 mL of a growth medium as described in Example 1. The test compounds were then tested and evaluated as in Example 1.

In accordance with the present invention, Table 3 shows that *S. aureus* (MN8), when compared to the control, produced significantly less TSST-1 in the presence of the aromatic compounds. The aromatic compounds reduced the amount of exotoxin production ranging from about 69% to 98%. However, although the amount of toxin produced was significantly reduced, there was minimal, if any, effect on the growth of *S. aureus* cells.

TABLE 3

| Compound | % Test Compound | Optical Density | CFU/mL | ELISA: TSST-1 ng/OD unit | Reduction of Toxin % |
|---|---|---|---|---|---|
| Growth Medium | Zero | 0.627 | 3.9E+09 | 1931 | N/A |
| Methanol | 100 uL | 0.588 | 5.2E+09 | 2041 | N/A |
| Phenylethyl alcohol | 0.5% | 0.476 | 5.5E+08 | 46 | 98% |
| Trans-cinnamic acid | 0.5% | 0.549 | 1.7E+09 | 436 | 82% |
| Acetyl tyrosine | 0.5% | 0.549 | 1.7E+09 | 436 | 69% |
| Gallic acid | 0.5% | 0.492 | 1.2E+09 | 63 | 95% |

N/A = Not Applicable

EXAMPLE 4

In this Example, the effect of various test compounds on the growth of *S. aureus* and the production of TSST-1 was determined. The effect of the test compounds tested in Example 4 was determined by placing the desired concentration, expressed in percent of the active compound, in 10 mL of a growth medium as described in Example 1. The test compounds were then tested and evaluated as in Example 1.

In accordance with the present invention, Table 4 shows that *S. aureus* (MN8), when compared to the control, produced significantly less TSST-1 in the presence of the aromatic compounds. The aromatic compounds reduced the amount of exotoxin production ranging from about 79% to 98%. However, although the amount of toxin produced was significantly reduced, there was minimal, if any, effect on the growth of *S. aureus* cells.

TABLE 4

| Compound | % Test Compound | Optical Density | CFU/mL | ELISA: TSST-1 ng/OD unit | Reduction of Toxin % |
|---|---|---|---|---|---|
| Growth Medium | Zero | 0.606 | 3.2E+09 | 1445 | N/A |
| Methanol | 100 µL | 0.567 | 1.3E+09 | 1151 | N/A |
| Phenylethyl alcohol | 0.5% | 0.554 | 5.4E+08 | 25 | 98% |
| 4-Acetamidophenol | 0.5% | 0.629 | 2.4E+09 | 230 | 79% |

N/A = Not Applicable

EXAMPLE 5

In this Example the growth of *S. aureus* and the production of TSST-1 in the presence of phenylethyl alcohol was measured using different TSST-1 producing strains of *S.* aureus. S. aureus FRI-1187 and FRI-1169 were obtained as lyophilized cultures from the stock collection of Dr. Merlin Bergdoll, Food Research Institute (Madison Wis.). The effect of the phenylethyl alcohol was determined by placing the desired concentration, expressed in percent of the active compound, in 10 mL of a growth medium as in Example 1. The phenylethyl alcohol was then tested and evaluated as in Example 1.

In accordance with the present invention, Table 5 shows that *S. aureus* when compared to the control, produced significantly less TSST-1 in the presence of the phenylethyl alcohol. The phenylethyl alcohol reduced the amount of exotoxin production from the FRI-1169 culture from about 95% to about 100%. The phenylethyl alcohol also significantly reduced the amount of exotoxin production from the FRI-1187 culture. However, although the amount of toxin produced was significantly reduced, there was minimal, if any, effect on the growth of *S. aureus* cells.

TABLE 5

| Compound | % Test Compound | Optical Density | CFU/mL | ELISA: TSST-1 ng/OD unit | Reduction of Toxin % |
|---|---|---|---|---|---|
| *S. aureus* FRI-11698 | | | | | |
| Growth medium | Zero | 1.068 | 1.11e+09 | 158 | N/A |
| Phenylethyl alcohol | 0.5% | 1.263 | 3.03E+08 | 2 | 99% |
| Phenylethyl alcohol | 0.25% | 1.208 | 2.05E+09 | 8 | 95% |
| *S. aureus* FRI-1187 | | | | | |
| Growth medium | Zero | 1.056 | 1.59E+09 | 92 | N/A |
| Phenylethyl alcohol | 0.5% | 1.296 | 2.55E+08 | none detected | 100% |
| Phenylethyl alcohol | 0.25% | 1.244 | 1.80E+09 | 1 | 98% |

N/A = Not Applicable

EXAMPLE 6

In this Example, the effect of test compounds in combination with surface active agents was evaluated utilizing a checkerboard experimental design. This allowed the evaluation of the interaction of two test compounds on the growth of *S. aureus* and the production of TSST-1. Four concentrations of one test compound (including zero) were combined with five concentrations of a second test compound (including zero) in test tubes. In this Example, phenyethyl alcohol (0%, 0.5%, 0.3%, 0.15%, and 0.05%) was combined with Cetiol 1414E (myreth-3 myristate) (10 mM, 5 mM, 2.5 mM and 0). The test solutions were otherwise prepared as described in Example 1 and evaluated in the same manner as Example 1.

As Table 6 below indicates, at every concentration of Cetiol 1414E, the phenylethyl alcohol increased the inhibition of production of TSST-1, and vice versa. The effect appears to be additive.

TABLE 6

| Cetiol 1414E | PEA (%) | ng TSST-1 per mL | CFU/mL | Log CFU/mL | ng TSST-1 per CFU | Reduction of Toxin % |
|---|---|---|---|---|---|---|
| 0 | 0.5 | 106 | 3.95E+08 | 8.6 | 27 | 93% |
| 0 | 0.3 | 201 | 5.15E+08 | 8.7 | 39 | 90% |
| 0 | 0.15 | 561 | 4.35E+08 | 8.6 | 129 | 67% |
| 0 | 0.05 | 826 | 3.10E+08 | 8.5 | 266 | 32% |
| 0 | 0 | 1178 | 3.00E+08 | 8.5 | 393 | 0% |
| 10 mM | 0.5 | 20 | 4.70E+08 | 8.7 | 4 | 99% |
| 10 mM | 0.3 | 59 | 7.20E+08 | 8.9 | 8 | 98% |
| 10 mM | 0.15 | 137 | 4.30E+08 | 8.6 | 32 | 92% |
| 10 mM | 0.05 | 240 | 4.60E+08 | 8.7 | 52 | 87% |
| 10 mM | 0 | 262 | 4.30E+08 | 8.6 | 61 | 84% |
| 5 mM | 0.5 | 58 | 6.25E+08 | 8.8 | 9 | 98% |
| 5 mM | 0.3 | 155 | 4.00E+08 | 8.6 | 39 | 90% |
| 5 mM | 0.15 | 348 | 4.10E+08 | 8.6 | 85 | 78% |
| 5 mM | 0.05 | 538 | 4.75E+08 | 8.7 | 113 | 71% |
| 5 mM | 0 | 558 | 3.25E+08 | 8.5 | 172 | 56% |
| 2.5 mM | 0.5 | 76 | 6.90E+08 | 8.8 | 11 | 97% |
| 2.5 mM | 0.3 | 197 | 2.80E+08 | 8.4 | 70 | 82% |
| 2.5 mM | 0.15 | 384 | 4.95E+08 | 8.7 | 78 | 80% |
| 2.5 mM | 0.05 | 618 | 4.15E+08 | 8.6 | 149 | 62% |
| 2.5 mM | 0 | 765 | 3.20E+08 | 8.5 | 239 | 39% |

EXAMPLE 7

In this Example, the effect of phenylethyl alcohol and 4-hydroxybenzoic acid, methyl ester on the production of alpha-toxin from *S. aureus* strain RN 6390 was evaluated utilizing a standard hemolytic assay.

The *S. aureus* alpha-toxin is a hemolytic exoprotein that causes target cell membrane damage and cell death. It is produced under environmental conditions similar to those seen with TSST-1 production. The effect of the test compounds on the growth of *S. aureus* and the production of alpha-toxin was carried out by placing the desired concentrations, expressed in percent of the active compound, in 100 mL of growth medium in 500 mL fleakers capped with aluminum foil. The growth medium and inoculum were prepared as described in Example 1. The fleakers were incubated in a 37° C. water bath with a gyratory shaker set at 180 rpm. Growth was followed by periodic optical density measurements at 600 nm. When the growth obtained an optical density of 1.0, 10 mL aliquots were removed for analysis. Plate counts were performed on the aliquots to determine cell count and culture purity. The remaining culture fluid was centrifuged at 2500 rpm for 15 minutes and the resulting supernatant filter sterilized and frozen at −70° C. until assayed.

Defibrinated rabbit red blood cells (Hema Resources, Aurora, Oreg.) were washed 3 times in Tris-saline buffer and re-suspended to a concentration of 0.5% (volume/volume). The Tris-saline buffer consisted of 50 mM Trizma® hydrochloride/Trizma base and 100 mM sodium chloride, with a final pH of 7.0. Culture supernatants were serially diluted in Tris-saline buffer from 1:2 to 1:256. One hundred microliters of each dilution was added to nine hundred microliters of the rabbit red blood cells. Each dilution was set up in triplicate. The tubes were incubated for 30 minutes at 37° C. The samples were then centrifuged at 800×g for 6 minutes. Two two-hundred microliter aliquots of each tube were transferred to a microtiter plate and the optical density determined at 410 nm. Control fluids used in place of the culture supernatants included tris-saline buffer (zero lysis), 10% sodium dodecyl sulfate (100% lysis), and sterile growth medium containing the test compound. Units of activity are expressed as the reciprocal of the dilution of each test sample giving 50% lysis in samples that were adjusted to the same initial optical density. As Tables 7 and 8 below indicate both phenylethyl alcohol and 4-hydroxybenzoic acid methyl ester significantly reduced production of alpha toxin.

TABLE 7

| Test Compound | % Test Compound | Hemolytic Endpoint 50% lysis | % Toxin Inhibition |
|---|---|---|---|
| None | 0 | 103 | N/A |
| Phenylethyl alcohol | 0.3% | 3 | 97% |
| Phenylethyl alcohol | 0.4% | None Detected | 100% |

N/A = Not Applicable

TABLE 8

| Test Compound | % Test Compound | Hemolytic Endpoint 50% lysis | % Toxin Inhibition |
|---|---|---|---|
| None | 0 | 265 | N/A |
| 4-hydroxybenzoic acid methyl ester | 0.1% | 79 | 70% |
| 4-hydroxybenzoic acid methyl ester | 0.2% | 16 | 94% |

N/A = Not Applicable

EXAMPLE 8

In this Example, the effect of phenylethyl alcohol in combination with Glucopon was evaluated utilizing a checkerboard experimental design. This allowed the evaluation of the interaction of two test compounds on the growth of *S. aureus* and the production of TSST-1.

Five concentrations of phenylethyl alcohol (0.5%, 0.3%, 0.15%, 0.05%, and 0.0%) were combined with four concentrations of Glucopon (1.5 mM, 0.75 mM, 0.25 mM and 0 mM) in a twenty tube array. For example, tube #1 contained 0 mM of Glucopon and 0.5% phenylethyl alcohol (vol/vol) in 10 mL of growth medium (as prepared in Example 1). Each of tubes #1–#20 contained a unique combination of Glucopon and phenylethyl alcohol. These combinations were tested and evaluated as in Example 1. The effect of the test compounds on the growth of *S. aureus* and on the production of TSST-1 is shown in Table 9 below.

TABLE 9

| Glucopon | PEA (%) | OD | ng TSST-1/OD | CFU/mL | % Reduction |
|---|---|---|---|---|---|
| 0 mM | 0.0 | 0.685 | 755 | 9.05E+08 | N/A |
| 0 mM | 0.05 | 0.712 | 323 | 1.07E+09 | 57% |
| 0 mM | 0.15 | 0.730 | 152 | 2.59E+09 | 80% |
| 0 mM | 0.3 | 0.758 | 54 | 1.97E+09 | 93% |
| 0 mM | 0.50 | 0.721 | 13 | 2.15E+09 | 98% |
| 0.25 mM | 0.0 | 0.660 | 542 | 1.26E+09 | 28% |
| 0.25 mM | 0.05 | 0.690 | 351 | 2.05E+09 | 54% |
| 0.25 mM | 0.15 | 0.705 | 173 | 2.44E+09 | 77% |
| 0.25 mM | 0.3 | 0.797 | 48 | 2.20e+09 | 94% |
| 0.25 mM | 0.5 | 0.657 | 14 | 1.21E+09 | 98% |
| 0.75 mM | 0.0 | 0.701 | 599 | 9.55E+08 | 21% |
| 0.75 mM | 0.05 | 0.705 | 285 | 8.60E+08 | 62% |
| 0.75 mM | 0.15 | 0.743 | 148 | 9.75E+08 | 80% |
| 0.75 mM | 0.3 | 0.731 | 45 | 2.19E+09 | 94% |
| 0.75 mM | 0.5 | 0.099 | 0 | 4.51E+07 | 100% |
| 1.5 mM | 0.0 | 0.718 | 196 | 1.83E+09 | 74% |
| 1.5 mM | 0.05 | 0.730 | 132 | 1.97E+09 | 83% |
| 1.5 mM | 0.15 | 0.694 | 68 | 1.11E+09 | 91% |
| 1.5 mM | 0.3 | 0.390 | 28 | >5.00E+07 | 96% |
| 1.5 mM | 0.5 | 0.014 | 0 | no growth | N/A |

N/A = Not Applicable

As Table 9 below indicates, at every concentration of glucopon the phenylethyl alcohol increased the inhibition of production of TSST-1, and vice versa. The effect appears to be additive.

EXAMPLE 10

In this Example, the effect of Cetiol in combination with para-aminobenzoic acid was evaluated utilizing a checkerboard experimental design. This allowed the evaluation of the interaction of two test compounds on the growth of *S. aureus* and the production of TSST-1.

Five concentrations of para-aminobenzoic acid (0.05%, 0.09%, 0.19%, 0.38%, and 0.0%) were combined with four concentrations of Cetiol (2.5 mM, 5 mM, 10 mM and 0 mM) in a twenty tube array. For example, tube #1 contained 0% of para-aminobenzoic acid and 0 mM Cetiol (vol/vol) in 10 mL of growth medium (as prepared in Example 1). Each of tubes #1–#20 contained a unique combination of Cetiol and para-aminobenzoic acid. These combinations were tested and evaluated as in Example 1. The effect of the test compounds on the growth of *S. aureus* and on the production of TSST-1 is shown in Table 10 below.

TABLE 10

| Cetiol | PABA | OD | ng TSST-1/OD | CFU/mL | % Reduction |
|---|---|---|---|---|---|
| 0 mM | 0% | 0.517 | 4907 | 8.90E+08 | N/A |
| 0 mM | 0.05% | 0.546 | 5670 | 1.53E+09 | 0% |
| 0 mM | 0.09% | 0.558 | 3389 | 1.85E+09 | 31% |
| 0 mM | 0.19% | 0.599 | 1975 | 1.79E+09 | 60% |
| 0 mM | 0.38% | 0.589 | 1039 | 1.15E+09 | 79% |
| 2.5 mM | 0% | 0.637 | 3367 | 1.21E+09 | 31% |
| 2.5 mM | 0.05% | 0.632 | 2193 | 1.89E+09 | 55% |
| 2.5 mM | 0.09% | 0.616 | 2413 | 1.46E+09 | 51% |
| 2.5 mM | 0.19% | 0.611 | 2106 | 1.38E+09 | 57% |
| 2.5 mM | 0.38% | 0.612 | 891 | 1.31E+09 | 82% |
| 5 mM | 0% | 0.881 | 2419 | 8.25E+08 | 51% |
| 5 mM | 0.05% | 0.957 | 1942 | 4.75E+08 | 60% |
| 5 mM | 0.09% | 0.862 | 1875 | 8.25E+08 | 62% |
| 5 mM | 0.19% | 0.849 | 1048 | 8.90E+08 | 79% |
| 5 mM | 0.38% | 0.971 | 221 | 1.19E+09 | 95% |
| 10 mM | 0% | 0.976 | 2286 | 3.95E+08 | 53% |
| 10 mM | 0.05% | 1.317 | 1420 | 4.80E+08 | 71% |
| 10 mM | 0.09% | 1.266 | 1244 | 8.10E+08 | 75% |
| 10 mM | 0.19% | 0.806 | 674 | 6.00E+08 | 86% |
| 10 mM | 0.38% | 0.749 | 467 | 6.55E+08 | 90% |

N/A = Not Applicable

In view of the above, it will be seen that the several objects of the invention are achieved. As various changes could be made in the above-described compositions without departing from the scope of the invention, it is intended that all matter contained in the above description be interpreted as illustrative and not in a limiting sense.

What is claimed is:

1. A douche formulation for inhibiting production of exoprotein from Gram positive bacteria comprising a vaginal cleansing formulation comprising a pharmaceutically acceptable carrier and from about 0.2 millimoles/liter to about 50 millimoles/liter of benzyl alcohol, wherein the benzyl alcohol is effective in inhibiting the production of exoprotein from Gram positive bacteria, and wherein the vaginal cleansing formulation is for use in a vagina.

2. The douche formulation as set forth in claim 1, wherein the benzyl alcohol is effective in substantially inihibiting the production of Toxic Shock Syndrome Toxin-1 (TSST-1 from *Staphylococcus aureus* bacteria.

3. The douche formulation as set forth in claim 1, wherein the benzyl alcohol is effective in substantially inhibiting the production of Enterotoxin B and alpha hemolysin from *Staphylococcus aureus* bacteria.

4. The douche formulation as set forth in claim 1, wherein the benzyl alcohol is present in the vaginal cleansing formulation in an amount of from about 0.3 millimoles/liter to about 30 millimoles/liter.

5. The douche formulation as set forth in claim 1, wherein the benzyl alcohol is present in the vaginal cleansing formulation in an amount of from about 1 millimoles/liter to about 15 millimoles/liter.

* * * * *

UNITED STATES PATENT AND TRADEMARK OFFICE

CERTIFICATE OF CORRECTION

PATENT NO. : 7,026,354 B2
APPLICATION NO. : 09/969218
DATED : April 11, 2006
INVENTOR(S) : Rae Ellen Syverson et al.

It is certified that error appears in the above-identified patent and that said Letters Patent is hereby corrected as shown below:

Column 22, claim 2, line 52: "(TSST-1" should read -- (TSST-1) --.

Signed and Sealed this

Twenty-fourth Day of July, 2007

JON W. DUDAS
*Director of the United States Patent and Trademark Office*